(12) United States Patent
Nagai et al.

(10) Patent No.: US 8,486,594 B2
(45) Date of Patent: Jul. 16, 2013

(54) P-TERPHENYL COMPOUND MIXTURE AND ELECTROPHOTOGRAPHIC PHOTORECEPTORS MADE BY USING THE SAME

(75) Inventors: Shinya Nagai, Tokyo (JP); Atsushi Takesue, Fukushima (JP); Makoto Koike, Fukushima (JP); Katsumi Abe, Fukushima (JP); Takehiro Nakajima, Fukushima (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 826 days.

(21) Appl. No.: 12/161,964

(22) PCT Filed: Jan. 24, 2007

(86) PCT No.: PCT/JP2007/051103
§ 371 (c)(1),
(2), (4) Date: Jul. 24, 2008

(87) PCT Pub. No.: WO2007/086439
PCT Pub. Date: Feb. 8, 2007

(65) Prior Publication Data
US 2009/0053633 A1    Feb. 26, 2009

(30) Foreign Application Priority Data

Jan. 25, 2006  (JP) .................................. 2006-016623

(51) Int. Cl.
*G03G 5/06*   (2006.01)
(52) U.S. Cl.
USPC ..................... 430/58.8; 430/58.65; 430/58.75; 564/307; 564/433
(58) Field of Classification Search
USPC ................... 430/58.65, 58.75, 58.8; 564/307, 564/433
See application file for complete search history.

(56) References Cited

U.S. PATENT DOCUMENTS

| | | | | |
|---|---|---|---|---|
| 5,393,627 A | * | 2/1995 | Nakamura et al. | 430/58.5 |
| 6,787,277 B2 | * | 9/2004 | Tong et al. | 430/58.8 |
| 2002/0076632 A1 | * | 6/2002 | Yanus et al. | 430/58.75 |
| 2008/0076050 A1 | | 3/2008 | Abe et al. | |

FOREIGN PATENT DOCUMENTS

| | | |
|---|---|---|
| EP | 1 752 441 A1 * | 2/2007 |
| JP | 56 119132 | 9/1981 |
| JP | 61 129648 | 6/1986 |
| JP | 6 73018 | 9/1994 |
| JP | 07-324059 | 12/1995 |
| JP | 2002 275133 | 9/2002 |
| JP | 2004-026732 | 1/2004 |
| JP | 2004-262761 | 9/2004 |
| JP | 2005-166680 | 6/2005 |
| JP | 2005-314428 | 11/2005 |
| JP | 2006 285119 | 10/2006 |
| WO | 2005 115970 | 12/2005 |
| WO | 2006-006505 | 1/2006 |
| WO | WO 2006/057373 A1 | 6/2006 |

OTHER PUBLICATIONS

U.S. Appl. No. 12/569,012, filed Sep. 29, 2009, Abe, et al.
Extended European Search Report issued Jun. 20, 2012 in patent application No. 07707350.0.
Japanese Office Action issued Sep. 4, 2012 in corresponding Japanese Patent Application No. 2007-555983 with English translation (9 pp.).

* cited by examiner

*Primary Examiner* — Peter Vajda
(74) *Attorney, Agent, or Firm* — Oblon, Spivak, McClelland, Maier & Neustadt, L.L.P.

(57) ABSTRACT

An object of the invention is to provide: a p-terphenyl compound mixture useful as a charge-transporting agent which has improved solubility in organic solvents to thereby diminish a cracking phenomenon, which poses problems concerning photoreceptor characteristics, and can realize an electrophotographic photoreceptor having high sensitivity and high durability; and an electrophotographic photoreceptor employing the compound mixture. The invention relates to: a p-terphenyl compound mixture which includes two symmetric p-terphenyl compounds respectively represented by the following general formula (1) and general formula (2) and an asymmetric p-terphenyl compound represented by the following general formula (3) which has both a group of substituents of the compound represented by general formula (1) and a group of substituents of the compound represented by general formula (2); and an electrophotographic photoreceptor containing the compound mixture.

[Chem. 1]

(1)

[Chem. 2]

-continued (2)

[Chem. 3]

(3)

8 Claims, 5 Drawing Sheets

P-TERPHENYL COMPOUND MIXTURE AND ELECTROPHOTOGRAPHIC PHOTORECEPTORS MADE BY USING THE SAME

TECHNICAL FIELD

The present invention relates to a p-terphenyl compound mixture which has improved solubility in organic solvents to thereby diminish the cracking phenomenon caused by insufficient solubility and is useful as a charge-transporting agent in electrophotographic photoreceptors. The invention further relates to an electrophotographic photoreceptor employing the compound mixture.

BACKGROUND ART

Electrophotography is one type of image-forming technique which generally includes charging the surface of a photoreceptor containing a photoconductive material by, e.g., corona discharge in the dark, exposing the charged surface to light to selectively eliminate the charge in the exposed areas and thereby obtain an electrostatic latent image, developing the latent image with a toner, and then transferring and fixing the toner to paper or the like to obtain an image. Inorganic photoconductive substances such as selenium, zinc oxide, cadmium sulfide, and silicon have hitherto been used extensively in photoreceptors for electrophotography. Although these inorganic substances have many merits, they have had various drawbacks. For example, selenium has drawbacks that it necessities difficult production conditions and that selenium is apt to crystallize with heat or mechanical impact. Zinc oxide and cadmium sulfide have problems concerning moisture resistance and mechanical strength and further have a drawback that these substances deteriorate in suitability for charge or exposure by the action of a dye added as a sensitizer, resulting in poor durability. Silicon also necessitates difficult production conditions and further necessitates use of a highly irritant gas, resulting in a high cost. Silicon is sensitive to moisture and, hence, care should be taken in handling. In addition, selenium and cadmium sulfide have a problem concerning toxicity.

Organic photoreceptors which employ various organic compounds and in which those drawbacks of inorganic photoreceptors have been mitigated are in extensive use. The organic photoreceptors include single-layer type photoreceptors in which a charge-generating agent and a charge-transporting agent have been dispersed in a binder resin and multilayer type photoreceptors in which functions have been allotted to a charge-generating layer and a charge-transporting layer. Organic photoreceptors of the function allocation type are being extensively used because there is a wide choice from which each material can be selected and because a photoreceptor having any desired performances can be relatively easily produced by selecting a suitable combination.

As the charge-generating agent, many organic pigments and dyes have been proposed and put to practical use. Examples thereof include azo compounds, bisazo compounds, trisazo compounds, tetrakisazo compounds, thiapyrylium salts, squarylium salts, azulenium salts, cyanine dyes, perylene compounds, metal-free or metal phthalocyanine compounds, polycyclic quinone compounds, thioindigo compounds, and quinacridone compounds.

Examples of the charge-transporting agent include oxadiazole compounds (see, for example, patent document 1), oxazole compounds (see, for example, patent document 2), pyrazoline compounds (see, for example, patent document 3), hydrazone compounds (see, for example, patent documents 4 to 7), diamine compounds (see, for example, patent document 8), stilbene compounds (see, for example, patent documents 9 to 11), and butadiene compounds (see, for example, patent document 12). Organic photoreceptors employing these charge-transporting agents have excellent properties, and some of these have been put to practical use. However, an organic photoreceptor which fully satisfies various properties required of photoreceptors for electrophotography has not been obtained so far. Those charge-transporting agents include ones which have satisfactory properties including sensitivity but are poor in compatibility with resins and solubility in solvents and which hence have not been put to practical use.

Patent Document 1: JP-B-34-005466
Patent Document 2: JP-A-56-123544
Patent Document 3: JP-B-52-041880
Patent Document 4: JP-B-55-042380
Patent Document 5: JP-B-61-040104
Patent Document 6: JP-B-62-035673
Patent Document 7: JP-B-63-035976
Patent Document 8: JP-B-58-032372
Patent Document 9: JP-B-63-018738
Patent Document 10: JP-B-63-019867
Patent Document 11: JP-B-3-039306
Patent Document 12: JP-A-62-030255

Among the patent documents which have been filed, some disclose the use of a p-terphenyl compound in an electrophotographic photoreceptor (see, for example, patent documents 13 and 14). Patent document 13 discloses compounds including a p-terphenyl compound. The technique disclosed in this document is intended to improve electrophotographic characteristics including durability and sensitivity by incorporating the p-terphenyl compound into the charge-generating layer of a multilayer type photoreceptor. On the other hand, the p-terphenyl compound disclosed in patent document 14 has insufficient properties including durability, although excellent in solubility.

A charge-transporting agent for use in organic photoreceptors is required not only to enable the photoreceptors to satisfy electrical properties including sensitivity but also to have chemical stability which enables the agent to withstand light, ozone, and electrical load and stability or durability which prevents the photoreceptors from decreasing in sensitivity with repetitions of use or during long-term use. Furthermore, in producing an organic photoreceptor, high and stable solubility in solvents is necessary. However, no compound has been found which has excellent solubility, is excellent in stability and durability, and is satisfactory.

Patent Document 13: JP-A-61-129648
Patent Document 14: JP-B-6-073018

DISCLOSURE OF THE INVENTION

Problems that the Invention is to Solve

An object of the invention is to provide a p-terphenyl compound mixture useful as a charge-transporting agent which has improved solubility in organic solvents to thereby diminish a cracking phenomenon, which poses problems concerning photoreceptor characteristics, and can realize an electrophotographic photoreceptor having high sensitivity and high durability. Another object of the invention is to provide an electrophotographic photoreceptor employing the compound mixture.

Means for Solving the Problems

The invention relates to a p-terphenyl compound mixture which comprises two symmetric p-terphenyl compounds respectively represented by the following general formula (1) and general formula (2) and an asymmetric p-terphenyl compound represented by the following general formula (3) which has both a group of substituents of the compound represented by general formula (1) and a group of substituents of the compound represented by general formula (2):

[Chem. 1]

(1)

[Chem. 2]

(2)

[Chem. 3]

(3)

wherein R1, R2, R3, R4, R5, R6, R7, and R8 each independently represent a hydrogen atom, an alkyl group, an alkoxy group, an aralkyl group, a halogen atom, a di-substituted amino group, or a substituted or unsubstituted phenyl group, provided that R1 and R2, R3 and R4, R5 and R6, and R7 and R8 may collectively form a ring, and that the group of the substituents R5, R6, R7, and R8 differ from the group of the substituents R1, R2, R3, and R4 in at least one substituent or substitution position).

The invention further relates to a p-terphenyl compound mixture for electrophotographic photoreceptors which comprises two symmetric p-terphenyl compounds respectively represented by general formula (1) and general formula (2) given above and an asymmetric p-terphenyl compound represented by general formula (3) given above which has both the group of the substituents of the compound represented by general formula (1) and the group of the substituents of the compound represented by general formula (2).

The invention furthermore relates to an electrophotographic photoreceptor which includes a conductive support and, formed on the support, a layer containing the p-terphenyl compound mixture.

Advantages of the Invention

The p-terphenyl compound mixture of the invention has improved solubility in organic solvents and is effective in diminishing the cracking phenomenon. An electrophotographic photoreceptor can hence be provided which has an excellent drift mobility, satisfies photoreceptor characteristics, and has high sensitivity and high durability.

BRIEF DESCRIPTION OF THE REFERENCE NUMERALS

1 Conductive support
2 Charge-generating layer
3 Charge-transporting layer
4 Photosensitive layer
5 Undercoat layer
6 Layer containing charge-transporting substance
7 Charge-generating agent
8 Protective layer Best Mode for Carrying out the Invention

The p-terphenyl compound mixture of the invention, which comprises the two symmetric p-terphenyl compounds respectively represented by general formula (1) and general formula (2) given above and the asymmetric p-terphenyl compound represented by general formula (3) given above, can be synthesized from two diphenylamine compounds respectively represented by the following general formula (4) and general formula (5) and 4,4"-diiodo-p-terphenyl through a one-stage reaction, e.g., the Ullmann reaction.

[Chem. 4]

(4)

[Chem. 5]

(5)

In the formulae, R1, R2, R3, R4, R5, R6, R7, and R8 each independently represent a hydrogen atom, an alkyl group, an alkoxy group, an aralkyl group, a halogen atom, a di-substituted amino group, or a substituted or unsubstituted phenyl group, provided that R1 and R2, R3 and R4, R5 and R6, and R7 and R8 may collectively form a ring, and that the group of the substituents R5, R6, R7, and R8 differ from the group of the substituents R1, R2, R3, and in at least one substituent or substitution position.)

Specific examples of the symmetric p-terphenyl compound represented by general formula (1) or general formula (2) include the following compounds. In the invention, the symmetric compound should not be construed as being limited to the following compounds.

[Chem. 6]

Compound No. 1

[Chem. 7]

Compound No. 2

[Chem. 8]

Compound No. 3

[Chem. 9]

Compound No. 4

[Chem. 10]

Compound No. 5

[Chem. 11]

Compound No. 6

[Chem. 12]

Compound No. 7

[Chem. 13]

Compound No. 8

[Chem. 14]

Compound No. 9

[Chem. 15]

Compound No. 10

[Chem. 16]

Compound No. 11

[Chem. 17]

Compound No. 12

[Chem. 18]

Compound No. 13

[Chem. 19]

Compound No. 14

[Chem. 20]

Compound No. 15

[Chem. 21]

Compound No. 16

Specific examples of the asymmetric p-terphenyl compound represented by general formula (3) include the following compounds. In the invention, the asymmetric compound should not be construed as being limited to the following compounds.

[Chem. 22]

Compound No. 17

[Chem. 23]

Compound No. 18

[Chem. 24]

Compound No. 19

[Chem. 25]

Compound No. 20

In the p-terphenyl compound mixture of the invention, the content of the p-terphenyl compound represented by general formula (1) is desirably 50-80% by mass. It is more desirable that the mixture is a p-terphenyl compound mixture in which the content of the p-terphenyl compound represented by general formula (1) is 60-70% by mass. It is also desirable that the content of the p-terphenyl compound represented by general formula (3) in the p-terphenyl compound mixture of the invention is 2-48% by mass.

The electrophotographic photoreceptor of the invention contains a p-terphenyl compound mixture comprising p-terphenyl compounds respectively represented by general formula (1), general formula (2), and general formula (3) (provided that in the formulae, the group of the substituents R5, R6, R7, and R8 differ from the group of the substituents R1, R2, R3, and R4 in at least one substituent or substitution position). The content of the p-terphenyl compound represented by general formula (1) in the mixture is desirably 50-80% by mass, more desirably 60-70% by mass.

There are various forms of photosensitive layer. The photosensitive layer of the electrophotographic photoreceptor of the invention may have any of the forms. Photoreceptors employing typical examples of the various forms are shown in FIG. 1 to FIG. 7.

Figure 1:
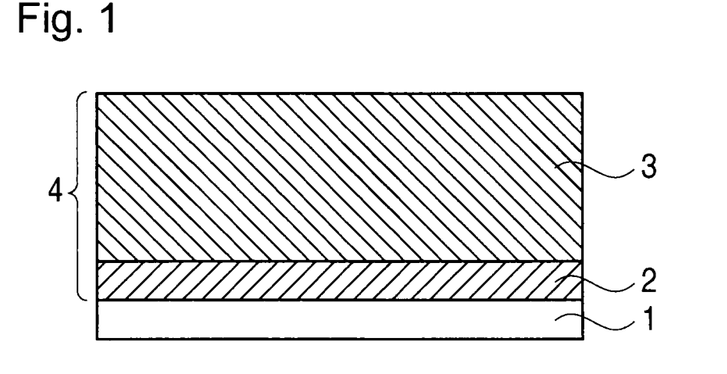
FIG. 1 is a diagrammatic sectional view illustrating the layer constitution of a function allocation type electrophotographic photoreceptor.
Figure 2:
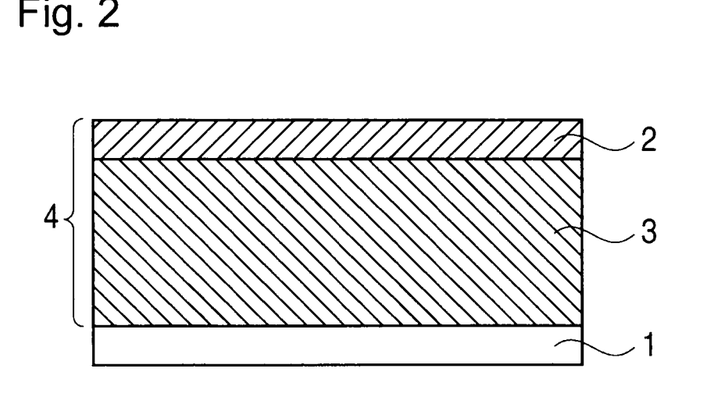
FIG. 2 is a diagrammatic sectional view illustrating the layer constitution of another function allocation type electrophotographic photoreceptor.
Figure 3:
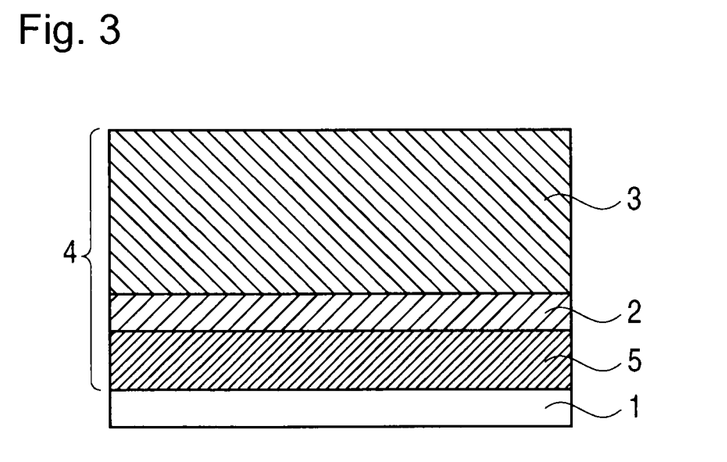
FIG. 3 is a diagrammatic sectional view illustrating the layer constitution of a function allocation type electrophotographic photoreceptor which has an undercoat layer formed between a charge-generating layer and a conductive support.
Figure 4:
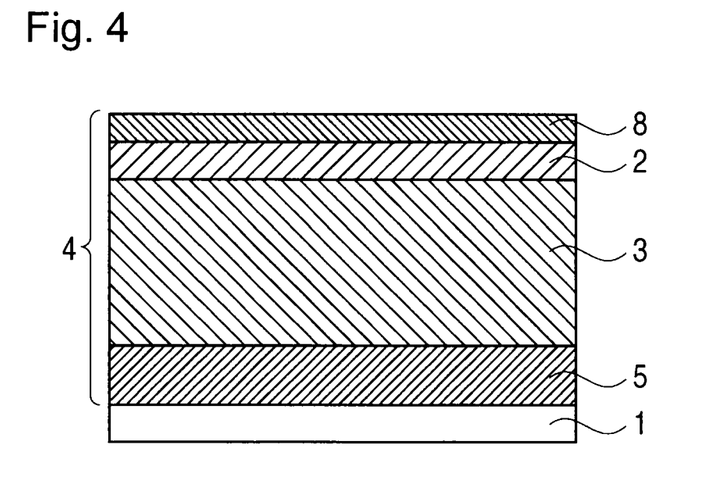
FIG. 4 is a diagrammatic sectional view illustrating the layer constitution of a function allocation type electrophotographic photoreceptor which has an undercoat layer formed between a charge-transporting layer and a conductive support and further has a protective layer formed on a charge-generating layer.
Figure 5:
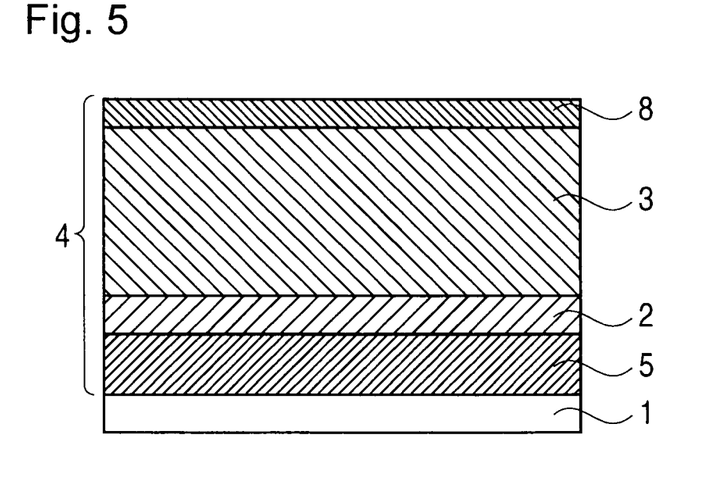
FIG. 5 is a diagrammatic sectional view illustrating the layer constitution of a function allocation type electrophotographic photoreceptor which has an undercoat layer formed between a charge-generating layer and a conductive support and further has a protective layer formed on a charge-transporting layer.
Figure 6:
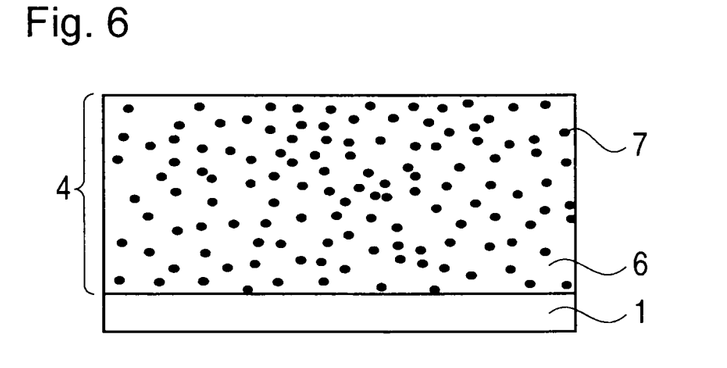
FIG. 6 is a diagrammatic sectional view illustrating the layer constitution of a single-layer type electrophotographic photoreceptor.
Figure 7:
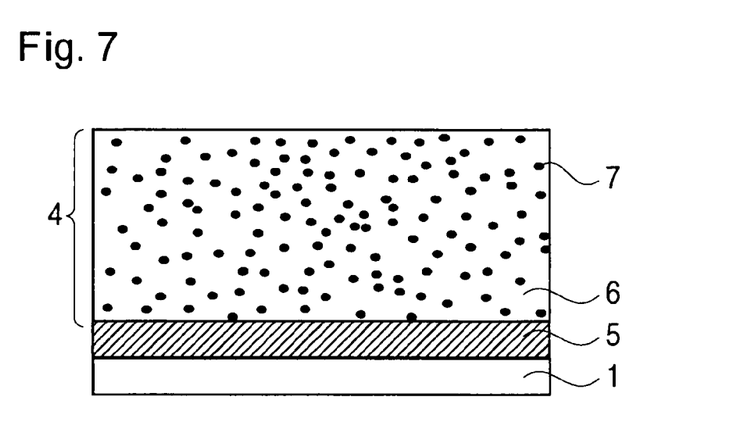
FIG. 7 is a diagrammatic sectional view illustrating the layer constitution of a single-layer type electrophotographic photoreceptor which has an undercoat layer formed between a photosensitive layer and a conductive support.

FIG. 1 and FIG. 2 show photoreceptors each constituted of a conductive support 1 and a photosensitive layer 4 formed thereon which has a multilayer structure composed of a charge-generating layer 2 containing a charge-generating substance as a main component and a charge-transporting layer 3 containing a charge-transporting substance and a binder resin as main components. In such constitutions, the photosensitive layer 4 may be formed via an undercoat layer 5 which is formed on the conductive support for charge regulation, as shown in FIG. 3, FIG. 4, and FIG. 5. A protective layer 8 may be formed as an outermost layer. Furthermore, in the invention, a photosensitive layer 4 constituted of a layer 6 which contains a charge-transporting substance and a binder resin as main components and further contains the charge-generating substance 7 dissolved or dispersed in the layer 6 may be formed directly or via an undercoat layer 5 on a conductive support 1 as shown in FIG. 6 and FIG. 7.

The photoreceptor of the invention, embodiments of which were shown above, may be produced by ordinary methods. For example, the photoreceptor can be produced by dissolving the p-terphenyl compound mixture described above, which comprises p-terphenyl compounds respectively represented by general formulae (1) to (3), in a solvent together with a binder resin, adding a charge-generating substance thereto optionally together with a sensitizing dye, electron-transporting compound, and electron-attracting compound and further with a plasticizer, pigment, and other additives to prepare a coating fluid, applying the coating fluid to a conductive support, and drying the coating to form a photosensitive layer having a thickness of from several micrometers to tens of micrometers. In the case of a photosensitive layer composed of two layers, i.e., a charge-generating layer and a charge-transporting layer, a photoreceptor can be produced by forming a charge-transporting layer containing the p-terphenyl compound mixture of the invention on a charge-generating layer or by forming a charge-generating layer on such a charge-transporting layer. According to need, an undercoat layer, adhesive layer, interlayer, and protective layer may be formed in the photoreceptor thus produced.

Examples of the solvent for coating fluid preparation include polar organic solvents such as tetrahydrofuran, 1,4-dioxane, methyl ethyl ketone, cyclohexanone, acetonitrile, N,N-dimethylformamide, and ethyl acetate, aromatic organic solvents such as toluene and xylene, and chlorinated hydrocarbon solvents such as dichloromethane and dichloroethane. It is preferred to use a solvent in which the p-terphenyl compound mixture described above, which comprises p-terphenyl compounds respectively represented by general formulae (1) to (3), and the binder resin are highly soluble.

Examples of the sensitizing dye include triarylmethane dyes such as Methyl Violet, Brilliant Green, Crystal Violet, and Acid Violet, xanthene dyes such as Rhodamine B, Eosin S, and Rose Bengal, thiazine dyes such as Methylene Blue, pyrylium dyes such as benzopyrylium salts, thiapyrylium dyes, and cyanine dyes.

Examples of the electron-attracting compound, which forms a charge-transfer complex in cooperation with the p-terphenyl compound mixture composed of p-terphenyl compounds represented by general formulae (1) to (3) include quinones such as chloranil, 2,3-dichloro-1,4-naphthoquinone, 1-nitroanthraquinone, 2-chloroanthraquinone, and phenanthrenequinone, aldehydes such as 4-nitrobenzaldehyde, ketones such as 9-benzoylanthracene, indanedione, 3,5-dinitrobenzophenone, 2,4,7-trinitrofluorenone, and 2,4,5,7-tetranitrofluorenone, acid anhydrides such as phthalic anhydride and 4-chloronaphthalic anhydride, cyano compounds such as tetracyanoethylene, terephthalalmalenonitrile, and 9-anthrylmethylidenemalenonitrile, and phthalides such as 3-benzalphthalide and 3-(α-cyano-p-nitrobenzal)-4,5,6,7-tetrachlorophthalide.

Examples of the binder resin include various resins compatible with the p-terphenyl compound mixture described above, which comprises p-terphenyl compounds respectively represented by general formulae (1) to (3), such as polymers and copolymers of vinyl compounds, e.g., styrene, vinyl acetate, vinyl chloride, acrylic esters, methacrylic esters, and butadiene, poly(vinyl acetal), polycarbonates, polyesters, poly(phenylene oxide), polyurethanes, cellulose esters, phenoxy resins, silicone resins, and epoxy resins. The amount of the binder resin to be used is generally in the range of 0.4-10 times by mass, preferably 0.5-5 times by mass, the amount of the p-terphenyl compound mixture described above, which comprises p-terphenyl compounds respectively represented by general formulae (1) to (3).

A known plasticizer may be incorporated into the photosensitive layer in the invention for the purpose of improving film-forming properties, flexibility, and mechanical strength. Examples of the plasticizer include phthalic esters, phosphoric esters, chlorinated paraffins, methylnaphthalene, epoxy compounds, and chlorinated fatty acid esters.

As the conductive support on which the photosensitive layer according to the invention is to be formed, materials used in known electrophotographic photoreceptors can be employed. Examples thereof include a drum or sheet of a metal such as aluminum, aluminum alloy, stainless steel, copper, zinc, vanadium, molybdenum, chromium, titanium, nickel, indium, gold, or platinum, a laminate of any of these metals, a support having a vapor-deposited coating of any of these metals, a plastic film, plastic drum, paper, or paper tube which has undergone a conductivity-imparting treatment including applying a conductive substance, such as a metal powder, carbon black, copper iodide, or polymeric electrolyte, together with an appropriate binder, a plastic film or plastic drum to which conductivity has been imparted by incorporating a conductive substance thereinto, or the like.

The invention will be illustrated in greater detail by reference to the following Examples. In the Examples, the "parts" are given by mass.

EXAMPLE 1

Synthesis Example 1

Synthesis of p-Terphenyl Compound Mixture Composed of Compounds No. 1, No. 18, and No. 9

The following ingredients were mixed together: 16.86 g (92 mmol) of 4-methyldiphenylamine, 3.89 g (23 mmol) of diphenylamine, 24.1 g (50 mmol) of 4,4"-diiodo-p-terphenyl, 17.25 g (125 mmol) of anhydrous potassium carbonate, 0.32 g (5 mmol) of a copper powder, 0.52 g (5 mmol) of sodium hydrogen sulfite, and 10 mL of sulfolane. The resultant mixture was heated to 220-225° C. and stirred for 6 hours while introducing nitrogen gas. After completion of the reaction, a reaction product was extracted with 90 mL of xylene and 150 mL of toluene, and the insoluble matter was removed by filtration. Thereafter, the filtrate was concentrated to dryness. The solid matter obtained was purified by column chromatography (support: silica gel, eluent: toluene:hexane=1:4). Thus, a p-terphenyl compound mixture composed of 4,4'-bis(4-methyldiphenylamino)-p-terphenyl (Compound No. 1), 4-(4-methyldiphenylamino)-4'-diphenylamino-p-terphenyl (Compound No. 18), and 4,4'-bis(diphenylamino)-p-terphenyl (Compound No. 9) in a ratio of Compound No. 1/Compound No. 18/Compound No. 9=65.8/30.5/3.4 (peak area ratio in high-performance liquid chromatography) was obtained in an amount of 25.78 g (yield: 87.8%, melting point: 157.2-159.2° C.).

The compounds were identified by singly synthesizing the individual compounds and comparing these compounds with the p-terphenyl compounds obtained above in retention time in high-performance liquid chromatography. Measuring conditions in the high-performance liquid chromatography conducted for compound identification and mixing ratio determination were as follows. Column, ODS column; eluent, tetrahydrofuran/methanol=1/10 (v/v); measuring wavelength, 254 nm.

Figure 8:
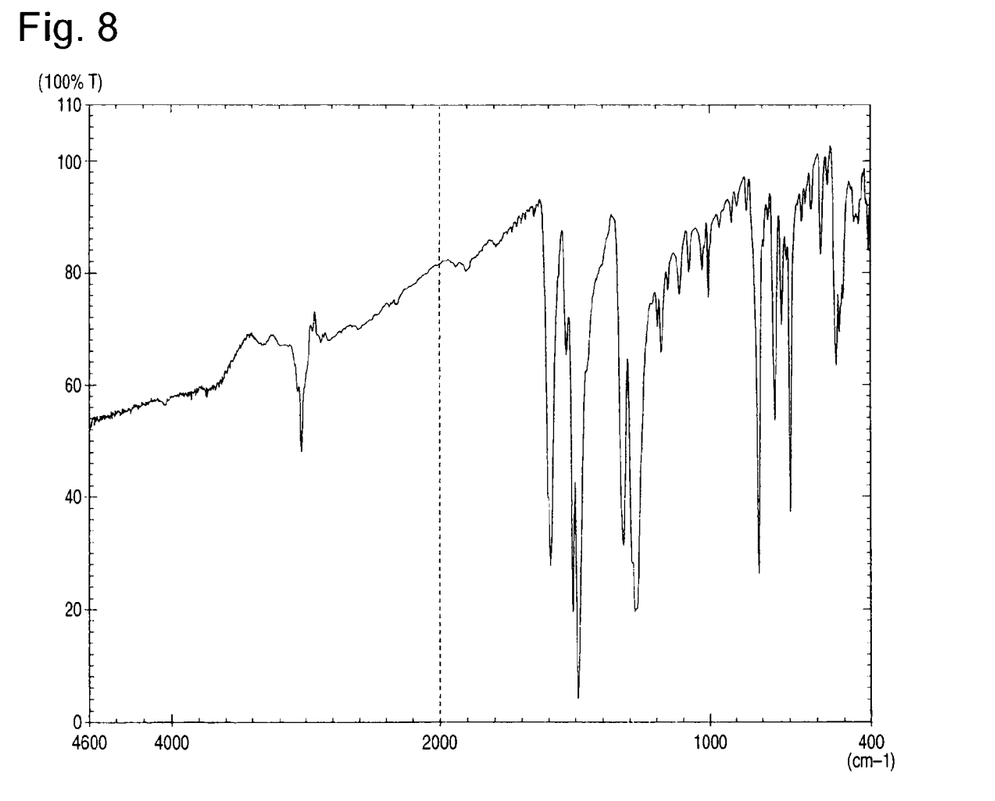
FIG. 8 is an IR spectrum obtained in Synthesis Example 1.

The compounds singly synthesized were identified by elemental analysis and were ascertained to be the respective target compounds. The found values in the elemental analysis were as follows. Compound No. 1: carbon, 89.13% (89.15%); hydrogen, 6.15% (6.12%); nitrogen, 4.72% (4.73%). Compound No. 18: carbon, 89.15% (89.24%); hydrogen, 5.98% (5.92%); nitrogen, 4.87% (4.84%). Compound No. 9: carbon, 89.24% (89.33%); hydrogen, 5.76% (5.71%); nitrogen, 5.00% (4.96%). (Calculated values are shown in the parentheses.) In FIG. 8 is shown an IR spectrum for the p-terphenyl compound mixture produced in Synthesis Example 1, which was composed of Compound No. 1, Compound No. 18, and Compound No. 9.

EXAMPLE 2

Synthesis Example 2

Synthesis of p-Terphenyl Compound Mixture Composed of Compounds No. 1, No. 17, and No. 4

The following ingredients were mixed together: 16.86 g (92 mmol) of 4-methyldiphenylamine, 4.53 g (23 mmol) of 2,4-dimethyldiphenylamine, 24.1 g (50 mmol) of 4,4"-diiodo-p-terphenyl, 17.25 g (125 mmol) of anhydrous potassium carbonate, 0.32 g (5 mmol) of a copper powder, 0.52 g (5 mmol) of sodium hydrogen sulfite, and 10 mL of sulfolane. The resultant mixture was heated to 220-225° C. and stirred for 6 hours while introducing nitrogen gas. After completion of the reaction, a reaction product was extracted with 90 mL of xylene and 150 mL of toluene, and the insoluble matter was removed by filtration. Thereafter, the filtrate was concentrated to dryness. The solid matter obtained was purified by column chromatography (support: silica gel, eluent: toluene:hexane=1:4). Thus, a p-terphenyl compound mixture composed of 4,4'-bis(4-methyldiphenylamino)-p-terphenyl (Compound No. 1), 4-(4-methyldiphenylamino)-4'-(2,4-dimethyldiphenylamino)-p-terphenyl (Compound No. 17), and 4,4'-bis(2,4-dimethyldiphenylamino)-p-terphenyl (Compound No. 4) in a ratio of Compound No. 1/Compound No. 17/Compound No. 4=69.0/27.2/2.9 (peak area ratio in high-performance liquid chromatography) was obtained in an amount of 26.65 g (yield: 89.1%, melting point: 174.1-177.0° C.).

The compounds were identified by singly synthesizing the individual compounds and comparing these compounds with the p-terphenyl compounds obtained above in retention time in high-performance liquid chromatography. Compound identification and mixing ratio determination were conducted under the high-performance liquid chromatography conditions described in Synthesis Example 1.

Figure 9:
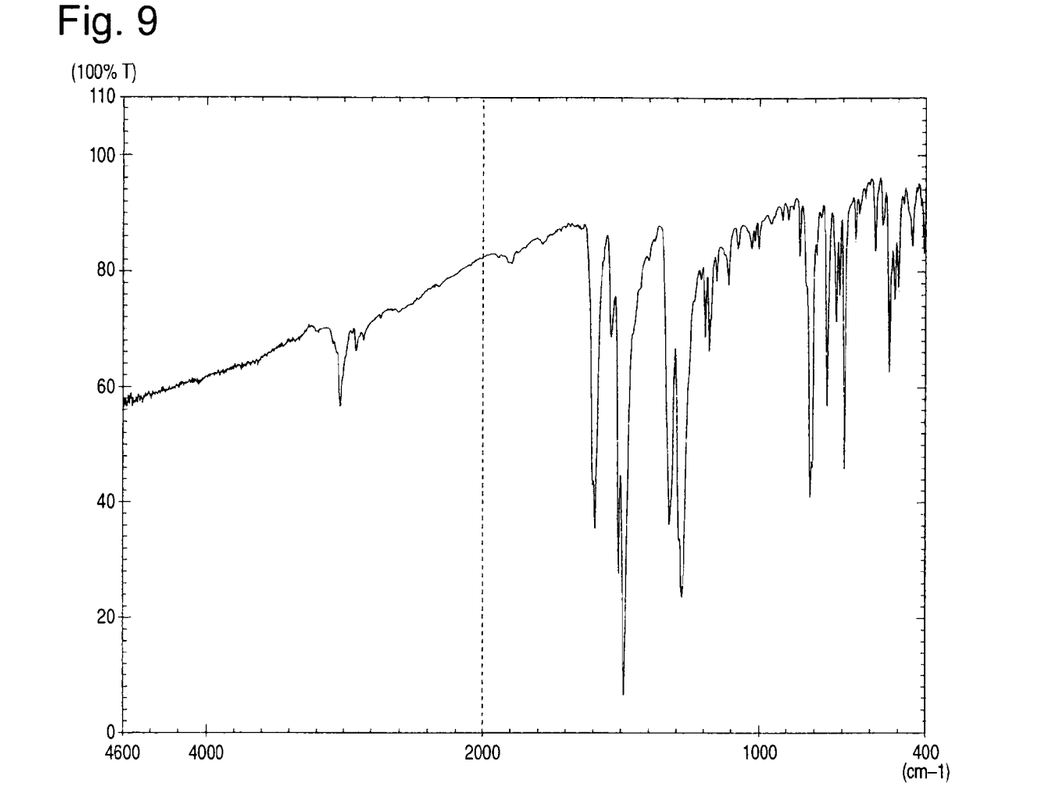
FIG. 9 is an IR spectrum obtained in Synthesis Example 2.

The compounds singly synthesized were identified by elemental analysis and were ascertained to be the respective target compounds. The found values in the elemental analysis were as follows. Compound No. 1: carbon, 89.13% (89.15%); hydrogen, 6.15% (6.12%); nitrogen, 4.72% (4.73%). Compound No. 17: carbon, 89.13% (89.07%); hydrogen, 6.41% (6.31%); nitrogen, 4.46% (4.62%). Compound No. 4: carbon, 89.04% (88.99%); hydrogen, 6.41% (6.49%); nitrogen, 4.55% (4.51%). (Calculated values are shown in the parentheses.) In FIG. 9 is shown an IR spectrum for the p-terphenyl compound mixture produced in Synthesis Example 2, which was composed of Compound No. 1, Compound No. 17, and Compound No. 4.

EXAMPLE 3

Synthesis Example 3

Synthesis of p-Terphenyl Compound Mixture Composed of Compounds No. 1, No. 19, and No. 6

The following ingredients were mixed together: 16.86 g (92 mmol) of 4-methyldiphenylamine, 4.53 g (23 mmol) of 4,4'-dimethyldiphenylamine, 24.1 g (50 mmol) of 4,4"-diiodo-p-terphenyl, 17.25 g (125 mmol) of anhydrous potassium carbonate, 0.32 g (5 mmol) of a copper powder, 0.52 g (5 mmol) of sodium hydrogen sulfite, and 10 mL of sulfolane. The resultant mixture was heated to 220-225° C. and stirred for 6 hours while introducing nitrogen gas. After completion of the reaction, a reaction product was extracted with 90 mL of xylene and 150 mL of toluene, and the insoluble matter was removed by filtration. Thereafter, the filtrate was concentrated to dryness. The solid matter obtained was purified by column chromatography (support: silica gel, eluent: toluene: hexane=1:4). Thus, a p-terphenyl compound mixture composed of 4,4'-bis(4-methyldiphenylamino)-p-terphenyl (Compound No. 1), 4-(4-methyldiphenylamino)-4'-(4,4'-dimethyldiphenylamino)-p-terphenyl (Compound No. 19), and 4,4'-bis(4,4'-dimethyldiphenylamino)-p-terphenyl (Compound No. 6) in a ratio of Compound No. 1/Compound No. 19/Compound No. 6=64.5/31.4/3.6 (peak area ratio in high-performance liquid chromatography) was obtained in an amount of 24.68 g (yield: 82.5%, melting point: 172.6-173.8° C.).

The compounds were identified by singly synthesizing the individual compounds and comparing these compounds with the p-terphenyl compounds obtained above in retention time in high-performance liquid chromatography. Compound identification and mixing ratio determination were conducted under the high-performance liquid chromatography conditions described in Synthesis Example 1.

Figure 10:
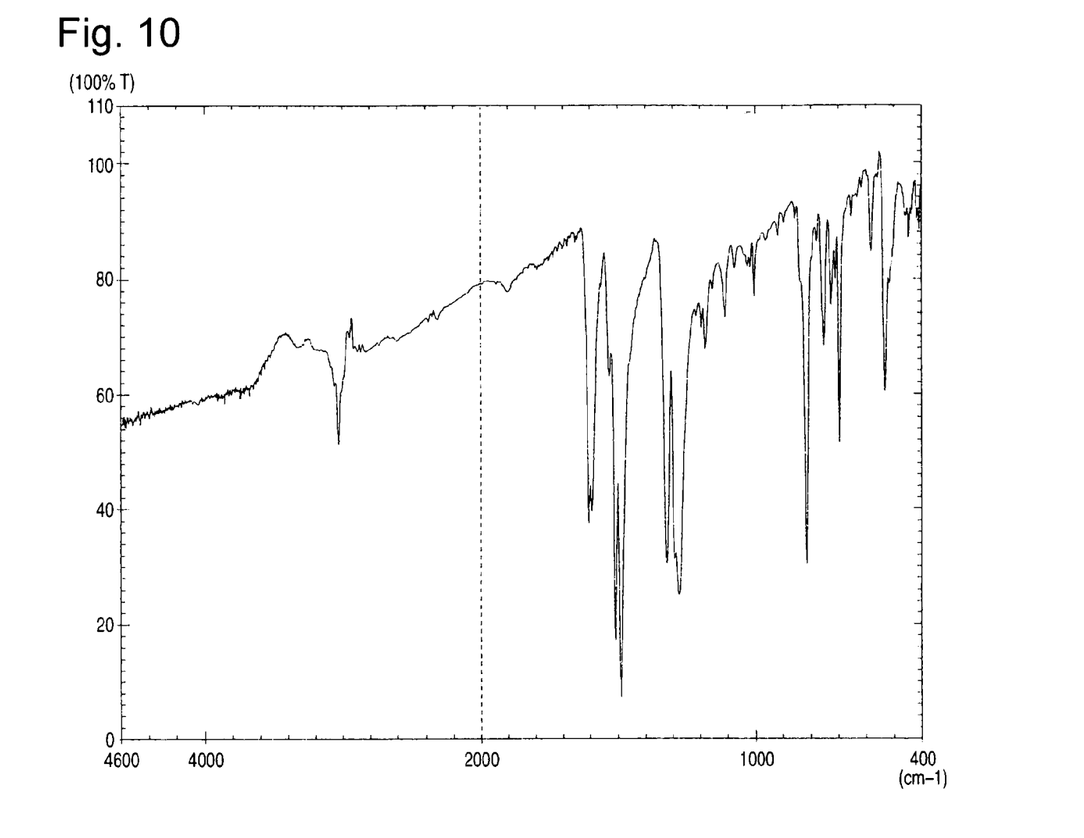
FIG. 10 is an IR spectrum obtained in Synthesis Example 3.

The compounds singly synthesized were identified by elemental analysis and were ascertained to be the respective target compounds. The found values in the elemental analysis were as follows. Compound No. 1: carbon, 89.13% (89.15%); hydrogen, 6.15% (6.12%); nitrogen, 4.72% (4.73%). Compound No. 19: carbon, 89.15% (89.07%); hydrogen, 6.42% (6.31%); nitrogen, 4.43% (4.62%). Compound No. 6: carbon, 89.02% (88.99%); hydrogen, 6.51% (6.49%); nitrogen, 4.47% (4.51%). (Calculated values are shown in the parentheses.) In FIG. 10 is shown an IR spectrum for the p-terphenyl compound mixture produced in Synthesis Example 3, which was composed of Compound No. 1, Compound No. 19, and Compound No. 6.

EXAMPLE 4

[Solubility in Organic Solvent]

The p-terphenyl compound mixtures obtained in Synthesis Examples 1 to 3 and p-terphenyl compounds singly synthesized (Compounds No. 1, No. 4, No. 6, and No. 9) were examined for solubility in 25° C. tetrahydrofuran. The results obtained are shown in Table 1. The unit of solubility is % (weight/volume).

TABLE 1

| Synthesis Example No. Compound No. | Solubility in tetrahydrofuran [%] |
|---|---|
| Synthesis Example 1 | 50.0 |
| Synthesis Example 2 | 75.2 |
| Synthesis Example 3 | 60.7 |
| Compound No. 1 | 25.0 |
| Compound No. 4 | 10.0 |
| Compound No. 6 | 2.0 |
| Compound No. 9 | 2.0 |

A comparison between the solubilities of the p-terphenyl compound mixtures according to the invention and those of the p-terphenyl compounds singly synthesized shows that the solubilities of the p-terphenyl compound mixtures were 2-38 times the solubilities of the p-terphenyl compounds singly synthesized. The p-terphenyl compound mixtures were ascertained to have excellent solubility.

EXAMPLE 5

Photoreceptor Example 1

In 13 parts of methanol was dissolved 1 part of an alcohol-soluble polyamide (Amilan CM-4000, manufactured by Toray Industries, Inc.). Thereto was added 5 parts of titanium oxide (Tipaque CR-EL, manufactured by Ishihara Sangyo Kaisha, Ltd.). The resultant mixture was treated with a paint shaker for 8 hours to disperse the titanium oxide and thereby produce a coating fluid for undercoat layer formation. Thereafter, the coating fluid was applied with a wire-wound bar to the aluminum side of a PET film having a vapor-deposited aluminum coating, and then dried at 60° C. for 1 hour to form an undercoat layer having a thickness of 1 μm.

Titanylphthalocyanine having a Cu-Kα X-ray diffraction spectrum having an intense peak at diffraction angles 2θ+0.2° of 9.6, 24.1, and 27.2 as a charge-generating agent (charge-generating agent No. 1)

[Chem. 26]

was added in an amount of 1.5 parts to 50 parts of a 3% cyclohexanone solution of a poly(vinyl butyral) resin (S-LEC BL-S, manufactured by Sekisui Chemical Co., Ltd.). The resultant mixture was treated with an ultrasonic disperser for 1 hour to disperse the charge-generating agent. The dispersion obtained was applied to the undercoat layer with a wire-wound bar and then dried at 110° C. and ordinary pressure for 1 hour to form a charge-generating layer having a thickness of 0.6 μm.

On the other hand, 1.5 parts of the p-terphenyl compound mixture synthesized in Synthesis Example 1 was added as a charge-transporting agent to 15.33 parts of a 12.2% tetrahydrofuran solution of a polycarbonate resin (Yupilon Z, manufactured by Mitsubishi Engineering-Plastic Corp.). The p-terphenyl compound mixture was completely dissolved by propagating an ultrasonic wave thereto. This solution was applied to the charge-generating layer with a wire-wound bar and dried at 110° C. and ordinary pressure for minutes to form a charge-transporting layer having a thickness of 20 μm. Thus, Photoreceptor No. 1 was produced.

EXAMPLE 6

Photoreceptor Examples 2 and 3

Photoreceptors Nos. 2 and 3 were produced in the same manner as in Photoreceptor Example 1, except that the p-terphenyl compound mixtures synthesized in Synthesis Examples 2 and 3 were used in place of the charge-transporting agent used in Photoreceptor Example 1.

Photoreceptor Comparative Example 1

Photoreceptor No. 4 was produced in the same manner as in Photoreceptor Example 1, except that the p-terphenyl compound singly synthesized as Compound No. 1 was used in place of the charge-transporting agent used in Photoreceptor Example 1.

Photoreceptor Comparative Example 2

Photoreceptor No. 5 was produced in the same manner as in Photoreceptor Example 1, except that the p-terphenyl compound singly synthesized as Compound No. 4 was used in place of the charge-transporting agent used in Photoreceptor Example 1.

Photoreceptor Comparative Example 3

Photoreceptor No. 6 was produced in the same manner as in Photoreceptor Example 1, except that the p-terphenyl compound singly synthesized as Compound No. 6 was used in place of the charge-transporting agent used in Photoreceptor Example 1. However, the p-terphenyl compound singly synthesized as Compound No. 6 did not dissolve and, hence, photoreceptor evaluation could not be made.

Photoreceptor Comparative Example 4

Photoreceptor No. 7 was produced in the same manner as in Photoreceptor Example 1, except that the p-terphenyl compound singly synthesized as Compound No. 9 was used in place of the charge-transporting agent used in Photoreceptor Example 1. However, the p-terphenyl compound singly synthesized as Compound No. 9 did not dissolve and, hence, photoreceptor evaluation could not be made.

EXAMPLE 7

The photoreceptors obtained in Photoreceptor Examples 1 to 3 and Photoreceptor Comparative Examples 1 to 4 were evaluated for electrophotographic properties with an electrostatic copying paper analyzer (trade name "EPA-8300A"). First, each photoreceptor was subjected to corona discharge at −6.5 kV in the dark, and the resultant charge potential V0 was measured. Subsequently, this photoreceptor was exposed to 780-nm monochromatic light at 1.0 μW/cm$^2$ to determine a half-decay exposure amount E1/2 (μJ/cm$^2$) and a residual potential after 5-second exposure Vr (−V). A cracking acceleration test for the photosensitive layer was further conducted in which finger grease was adhered to the surface of the photoreceptor produced above and this photoreceptor was allowed to stand for 24 hours at ordinary temperature and ordinary pressure to examine the photoreceptor as to whether the photosensitive layer cracked or not. The results obtained are shown in Table 2.

TABLE 2

| Example and Comparative Example | Photoreceptor No. | Charge potential $V_0$ (−V) | Half-decay exposure amount $E_{1/2}$ (μJ/cm$^2$) | Residual potential Vr (−V) | Cracking in photosensitive layer |
|---|---|---|---|---|---|
| Photoreceptor Example 1 | 1 | 834 | 0.25 | 15 | not occurred |
| Photoreceptor Example 2 | 2 | 825 | 0.25 | 18 | not occurred |
| Photoreceptor Example 3 | 3 | 838 | 0.24 | 15 | not occurred |
| Photoreceptor Comparative Example 1 | 4 | 836 | 0.25 | 13 | occurred |

TABLE 2-continued

| Example and Comparative Example | Photoreceptor No. | Charge potential $V_0$ (−V) | Half-decay exposure amount $E_{1/2}(\mu J/cm^2)$ | Residual potential Vr (−V) | Cracking in photosensitive layer |
|---|---|---|---|---|---|
| Photoreceptor Comparative Example 2 | 5 | 832 | 0.29 | 35 | occurred |
| Photoreceptor Comparative Example 3 | 6 | unable to be evaluated because the charge-transporting agent did not dissolve | | | |
| Photoreceptor Comparative Example 4 | 7 | unable to be evaluated because the charge-transporting agent did not dissolve | | | |

EXAMPLE 8

Photoreceptor Example 4

To 50 parts of a 3% cyclohexanone solution of a poly(vinyl butyral) resin (S-LEC BL-S, manufactured by Sekisui Chemical Co., Ltd.) was added 1.5 parts of titanylphthalocyanine having a Cu-Kα X-ray diffraction spectrum having an intense peak at diffraction angles 2θ+0.2° of 7.5, 10.3, 12.6, 22.5, 24.3, 25.4, and 28.6 as a charge-generating agent (charge-generating agent No. 2). The resultant mixture was treated with an ultrasonic disperser for 1 hour to disperse the charge-generating agent. The dispersion obtained was applied with a wire-wound bar to the aluminum side of a PET film, as a conductive support, which had a vapor-deposited aluminum coating. The dispersion applied was dried at 110° C. and ordinary pressure for 1 hour to form a charge-generating layer having a thickness of 0.2 μm.

On the other hand, 1.0 part the p-terphenyl compound mixture synthesized in Synthesis Example 1 was added as a charge-transporting agent to 10.22 parts of a 12.2% tetrahydrofuran solution of a polycarbonate resin (Yupilon Z, manufactured by Mitsubishi Engineering-Plastic Corp.). The p-terphenyl compound mixture was completely dissolved by propagating an ultrasonic wave thereto. This solution was applied to the charge-generating layer with a wire-wound bar and dried at 110° C. and ordinary pressure for 30 minutes to form a charge-transporting layer having a thickness of 10 μm. Furthermore, a semitransparent metal electrode was formed on the charge-transporting layer by vapor deposition to produce Photoreceptor No. 8.

EXAMPLE 9

Photoreceptor Examples 5 and 6

Photoreceptors Nos. 9 and 10 were produced in the same manner as in Photoreceptor Example 4, except that the p-terphenyl compound mixtures synthesized in Synthesis Examples 2 and 3 were used in place of the charge-transporting agent used in Photoreceptor Example 4.

Photoreceptor Comparative Examples 5 and 6

Photoreceptors Nos. 11 and 12 were produced in the same manner as in Photoreceptor Example 4, except that the p-terphenyl compound singly synthesized as Compound No. 1 or No. 4 was used in place of the charge-transporting agent used in Photoreceptor Example 4.

Photoreceptor Comparative Examples 7 and 8

Photoreceptors Nos. 13 and 14 were produced in the same manner as in Photoreceptor Example 4, except that the p-terphenyl compound singly synthesized as Compound No. 6 or No. 9 was used in place of the charge-transporting agent used in Photoreceptor Example 4. However, the p-terphenyl compound singly synthesized as Compound No. 6 or No. 9 did not dissolve and, hence, photoreceptor evaluation could not be made.

EXAMPLE 10

[Measurement of Drift Mobility]

The photoreceptors produced in Photoreceptor Examples 4 to 6 and Photoreceptor Comparative Examples 5 to were examined for drift mobility. A measurement was made by the time-of-flight method under the conditions of 2×105 (V/cm). The results obtained are shown in Table 3.

TABLE 3

| Example and Comparative Example | Photoreceptor No. | Drift mobility [cm$^2$/V · s] |
|---|---|---|
| Photoreceptor Example 4 | 8 | $6.9 \times 10^{-5}$ |
| Photoreceptor Example 5 | 9 | $6.8 \times 10^{-5}$ |
| Photoreceptor Example 6 | 10 | $7.1 \times 10^{-5}$ |
| Photoreceptor Comparative Example 5 | 11 | $6.7 \times 10^{-5}$ |
| Photoreceptor Comparative Example 6 | 12 | dispersive waveform |
| Photoreceptor Comparative Example 7 | 13 | unable to be evaluated because the charge-transporting agent did not dissolve |
| Photoreceptor Comparative Example 8 | 14 | unable to be evaluated because the charge-transporting agent did not dissolve |

As described above, the p-terphenyl compound mixture according to the invention has improved solubility in organic solvents. By using this compound mixture, a cracking phenomenon can be prevented. With the compound mixture, an electrophotographic photoreceptor having an excellent drift mobility, satisfying photoreceptor characteristics, and having high sensitivity and high durability can be provided.

While the invention has been described in detail and with reference to specific embodiments thereof, it will be apparent to one skilled in the art that various changes and modifications can be made therein without departing from the spirit and scope thereof.

This application is based on Japanese Patent Application No. 2006-016623 filed on Jan. 25, 2006, the contents thereof being herein incorporated by reference.

Industrial Applicability

The p-terphenyl compound mixture according to the invention has improved solubility in organic solvents and is useful as a charge-transporting agent capable of realizing an electrophotographic photoreceptor which is prevented from suffering a cracking phenomenon, satisfies photoreceptor characteristics, and has high sensitivity and high durability.

The invention claimed is:

1. A p-terphenyl compound mixture which consists of two symmetric p-terphenyl compounds respectively represented by formula (1) and formula (2) and an asymmetric p-terphenyl compound represented by formula (3) which has both a group of substituents of the compound represented by formula (1) and a group of substituents of the compound represented by formula (2):

wherein R1, R2, R3, R4, R5, R6, R7, and R8 each independently represent a hydrogen atom, an alkyl group, an alkoxy group, an aralkyl group, a halogen atom, a di-substituted amino group, or a substituted or unsubstituted phenyl group, provided that R1 and R2, R3 and R4, R5 and R6, and R7 and R8 may collectively form a ring, and that the group of the substituents R5, R6, R7, and R8 differ from the group of the substituents R1, R2, R3, and R4 in at least one substituent or substitution position.

2. The p-terphenyl compound mixture according to claim 1, wherein the content of the p-terphenyl compound represented by formula (1) is 50-80% by mass.

3. A p-terphenyl compound mixture for electrophotographic photoreceptors which consists of two symmetric p-terphenyl compounds respectively represented by formula (1) and formula (2) and an asymmetric p-terphenyl compound represented by formula (3) which has both a group of substituents of the compound represented by formula (1) and a group of substituents of the compound represented by formula (2):

wherein R1, R2, R3, R4, R5, R6, R7, and R8 each independently represent a hydrogen atom, an alkyl group, an alkoxy group, an aralkyl group, a halogen atom, a di-substituted amino group, or a substituted or unsubstituted phenyl group, provided that R1 and R2, R3 and R4, R5 and R6, and R7 and R8 may collectively form a ring, and that the group of the substituents R5, R6, R7, and R8 differ from the group of the substituents R1, R2, R3, and R4 in at least one substituent or substitution position.

4. The p-terphenyl compound mixture for electrophotographic photoreceptors according to claim 3, wherein the content of the p-terphenyl compound represented by formula (1) is 50-80% by mass.

5. An electrophotographic photoreceptor which has a layer containing the p-terphenyl compound mixture according to claim 1.

6. The electrophotographic photoreceptor according to claim 5, wherein the content of the p-terphenyl compound represented by formula (1) in the p-terphenyl compound mixture is 50-80% by mass.

7. A method of producing an electrophotographic photoreceptor, comprising incorporating the p-terphenyl compound mixture according to claim 1 in at least one of the layers of the electrophotographic photoreceptor.

8. The method of producing an electrophotographic photoreceptor according to claim 7, wherein the content of the p-terphenyl compound represented by formula (1) in the p-terphenyl compound mixture is 50-80% by mass.

* * * * *